(12) United States Patent
Huh et al.

(10) Patent No.: US 8,357,786 B2
(45) Date of Patent: Jan. 22, 2013

(54) **METHOD FOR PREPARING *GYNOSTEMMA PENTAPHYLLUM* EXTRACT WITH INCREASING DAMULIN A AND DAMULIN B CONTENTS, AND PHARMACEUTICAL COMPOSITIONS OF THE SAME FOR TREATING METABOLIC DISEASE**

(75) Inventors: Tae Lin Huh, Daegu (KR); He Bok Song, Seoul (KR); Ji Eun Kim, Daegu (KR); So Young Joon, Daegu (KR); Won Keun Oh, Kwangju (KR)

(73) Assignee: TG Biotech Co., Ltd., Daegu (KR)

( * ) Notice: Subject to any disclaimer, the term of this patent is extended or adjusted under 35 U.S.C. 154(b) by 210 days.

(21) Appl. No.: 12/696,362

(22) Filed: Jan. 29, 2010

(65) Prior Publication Data

US 2011/0015142 A1    Jan. 20, 2011

(30) Foreign Application Priority Data

Jul. 17, 2009    (KR) ........................ 10-2009-0065461

(51) Int. Cl.
  *C07G 3/00*    (2006.01)
  *C07H 17/00*    (2006.01)
  *A01N 45/00*    (2006.01)
(52) U.S. Cl. .............................. 536/18.5; 536/6; 514/26
(58) Field of Classification Search .................. None
  See application file for complete search history.

(56) References Cited

FOREIGN PATENT DOCUMENTS

| | | |
|---|---|---|
| JP | 2005-314421 A | 11/2005 |
| JP | 2006-124355 A | 5/2006 |
| JP | 2006-241097 A | 9/2006 |
| JP | 2008-222697 A | 9/2008 |
| JP | 2009-501696 A | 1/2009 |
| JP | 2009-040744 A | 2/2009 |
| WO | 2006/114775 A2 | 11/2006 |
| WO | WO 2006114775 A2 * | 11/2006 |

OTHER PUBLICATIONS

Wang et al. Carbohydrate Polymers 68 (2007) 54-58.*
Office Action issued in Japanese Patent Application No. 2010-015020 dated Sep. 18, 2012, along with English translation, 8 pages.
W. Kim et al.: "Steaming of Ginseng at High Temperature Enhances Biological Activity," J. Nat. Prod., vol. 63, No. 12, 2000, pp. 1702-1704.

* cited by examiner

*Primary Examiner* — Layla Bland
(74) *Attorney, Agent, or Firm* — Rothwell, Figg, Ernst & Manbeck, P.C.

(57) ABSTRACT

Disclosed is an AMPK activating material used for improving and treating metabolic syndrome, in which AMPK (AMP-activated protein kinase) is a main enzyme for regulating an energy sensor and lipid/glucose metabolism in the body. The activation of AMPK inhibits the synthesis of fat and cholesterol, and accelerates the reduction of body fat and blood glucose, thereby improving obesity, diabetes, and hyperlipidaemia. The disclosed AMPK activating material contains, as active ingredients having an improving and treating effect on metabolic syndrome, including obesity, diabetes, and hyperlipidaemia, a novel compound $2\alpha,3\beta,12\beta$-trihydroxydammar-20(22)-E,24-diene-3-O-[$\beta$-D-glucopyranosyl-(1→)-$\beta$-D-glucopyranoside], named Damulin A, and a novel compound $2\alpha,3\beta,12\beta$-trihydroxydammara-20,24-diene-3-O-[$\beta$-D-glucopyranosyl-(1→)-$\beta$-D-glucopyranoside], named Damulin B. Herein, the contents of damulin A and damulin B (as active indicator ingredients for AMPK activation) can be increased by treating a *Gynostemma pentaphyllum* extract with high temperature/high pressure. Accordingly, the novel *Gynostemma pentaphyllum* extract with a significantly increased AMPK activating capability can be used for improving or treating metabolic syndrome, such as obesity, diabetes, and hyperlipidaemia.

17 Claims, 5 Drawing Sheets

Control : Saline Solution)
L6 myotube cells

Control : Saline Solution)
L6 myotube cells

Figure 7

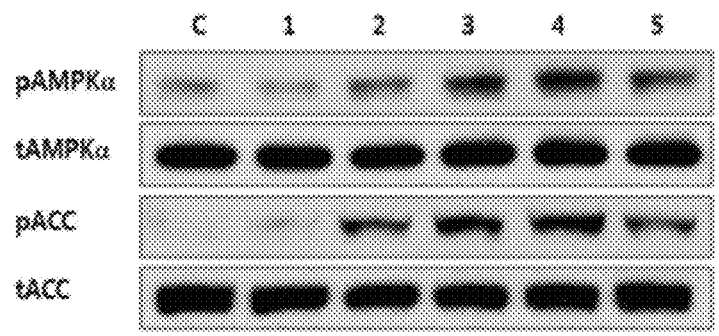

C: Negative Control – Saline Solution
1: TG1822 – 120 µg/ml
2: TG1822F – 60 µg/ml
3: TG1822F – 90 µg/ml
4: TG1822F – 120 µg/ml
5: Positive Control – Metformin(2mM)

TG1822: Normal Extract of *G. pentaphyllum*
TG1822F: Concentrated Extract of *G. pentaphyllum*

L6 myotube cells

Figure 8

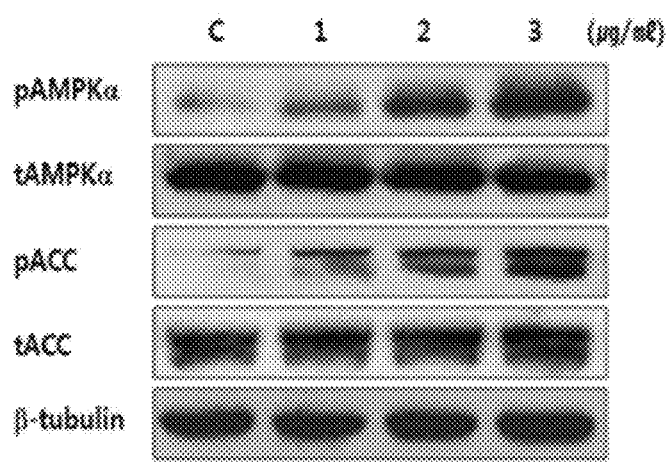

C: Negative Control – Saline Solution
1: TG1822 (300 mg/kg)
2: TG1822F (150 mg/kg)
3: TG1822F (300 mg/kg)

pAMPKα: phosphorylated AMPKα
tAMPKα: total AMPKα
pACC: phosphorylated ACC
tACC: total ACC Soleus muscle cells of mouse

METHOD FOR PREPARING *GYNOSTEMMA PENTAPHYLLUM* EXTRACT WITH INCREASING DAMULIN A AND DAMULIN B CONTENTS, AND PHARMACEUTICAL COMPOSITIONS OF THE SAME FOR TREATING METABOLIC DISEASE

CROSS REFERENCE TO RELATED APPLICATIONS

This application claims priority from Korean patent application No. 10-2009-0065461 filed on Jul. 17, 2009, all of which is incorporated herein by reference in its entirety for all purposes.

BACKGROUND OF THE INVENTION

1. Field of the Invention

The present invention relates to a method for preparing a novel composition-containing *Gynostemma pentaphyllum* extract, in which a *Gynostemma pentaphyllum* extract is treated with high temperature and high pressure, thereby increasing contents of damulin A and damulin B (active ingredients for AMPK activation).

Also, the present invention relates to a method for using a novel *Gynostemma pentaphyllum* extract with a novel composition having increased contents of damulin A and damulin B to efficiently treat and improve metabolic syndrome including obesity, diabetes, hyperlipidaemia, or the like.

2. Description of the Prior Art

AMPK (AMP-activated protein kinase) is a heterotrimer protein, consisting of α, β, γ subunit, and exists generally in muscle cells in abundance, and also in brain, heart, adipose tissue, and liver. AMPK functions as an important sensor that senses an energy level within cells, and thereby plays an important role in appetite regulation, weight regulation, blood glucose regulation, and blood lipid metabolism regulation, or the like.

When ATP consumption increases AMP concentration by intensive exercise or prolonged starvation, AMP is coupled to γ-subunit of AMPK, thereby activating AMPK. The activation actually occurs through the phosphorylation of a threonine residue at (Thr)-172 of AMPK alpha subunit by a superordinate phosphorylation enzyme, such as LKB1 or CaMKK.

Phosphorylated AMPK inhibits the synthesis of fatty acid and cholesterol, which is an ATP-consuming biochemical reaction, but activates β-oxidation of fatty acid and glycolysis, which generates ATP. Moreover, it increases the content of glucose transporter 4 (GLUT4) which is a glucose absorbing pathway toward a cell membrane. Meanwhile, regardless of PI3K signaling mechanism by insulin action, the activation of AMPK increases the movement of GLUT4 (intracellular glucose absorbing pathways) toward a cell membrane. Also, once AMPK is activated by phosphorylation, HMG-CoA reductase (hydroxymethylglutaryl-CoA reductase) that is another subordinate protein and is a main enzyme for cholesterol synthesis, is phosphorylated. As a result, the HMG-CoA reductase is inactivated, which lowers the cholesterol synthesis, thereby reducing blood cholesterol.

Also, the AMPK enzyme activated by phosphorylation phosphorylates a serine residue at (Ser)-79 of ACC (acetyl-CoA carboxylase) which is a subordinate protein and a main enzyme for fatty acid synthesis, thereby inhibiting the enzymatic activity of ACC. As a result, the activation of AMPK reduces the generation of malonyl-CoA that is a main metabolite for fatty acid synthesis, thereby inhibiting the fatty acid synthesis. The malonyl-CoA is reduced by the activation of AMPK, long chain acyl-CoA (fatty acid) is delivered into mitochondria, thereby accelerating beta oxidation. In the state where malonyl-CoA with high concentration exists, CPT1 (carnitine palmitoyl-CoA transferase) transferring long chain acyl-CoA to mitochondria is inhibited. Meanwhile, such an inhibition operation is canceled by reduction of the concentration of malonyl-CoA due to the activation of AMPK, and thereby the introduction of fatty acids of long chain acyl-CoA into mitochondria is increased. This increases beta oxidation, thereby reducing the body fat and blood neutral lipid.

Meanwhile, the activation of AMPK causes the phosphorylation of PGC-1α (Peroxisome proliferator-activated receptor gamma coactivator-1α), and also activates SIRT1 (Silent Information Regulatory T1) that is a kind of histone deacetylase. Accordingly, PGC-1α is phosphorylated and deacetylated by AMPK and SITR1, thereby activating mitochondria metabolism. This results in an improving effect of diabetes and obesity (Canto and Auwerx, Curr. Opin. Lipidol. 20, 98-105, 2009; Canto et al., Nature 458, 1056-1060, 2009). In other words, since the activation of AMPK inhibits the synthesis of fatty acid and cholesterol in the body, and accelerates the beta oxidation of body fat and cells' blood glucose absorption, any material capable of activating AMPK can be very effectively used for the improvement and treatment of obesity, diabetes, and hyperlipidaemia.

*Gynostemma pentaphyllum* is a perennial vine of the family Cucurbitaceae, which naturally grows in forests of mountains or fields. The *Gynostemma pentaphyllum* grows getting tangled by its rhizomes which extend to the side direction and have joints with white hair, or climbs by its tendrils. A tea obtained by drying *Gynostemma pentaphyllum* leaves is generally called a *Gynostemma pentaphyllum* extract tea, which removes alopecia greata, restores the functions of several internal organs, and maintains healthy skin. Also, the tea has an anti-stress effect, an atonic/spastic constipation inhibiting effect, an antidiarrhoeal effect, and the like, and is effective in bronchial asthma, senile chronic bronchitis, and the like. Also, the tea is known to have an antitussive expectorant function, a hepatitis/arteriosclerosis prevention function, and a pain relieving function, and to be effective in stress ulcer.

Korean Laid-Open Publication Patent No. 2008-0003931 discloses that a *Gynostemma pentaphyllum* extract can improve metabolic syndrome, including insulin resistance, obesity, and hyperlipidaemia, by increasing the activity of AMP-activated protein kinase (AMPK). Accordingly, through the analysis of the components of the *Gynostemma pentaphyllum* extract in the present invention, it was found that damulin A and damulin B included in the *Gynostemma pentaphyllum* extract are influential in the activity of AMPK. Also, the novel *Gynostemma pentaphyllum* extract with a novel composition having increased contents of damulin A and damulin B, according the method of the present invention, was determined to have a better capability for phosphorylation and enzymatic activation of AMPK, than a conventional *Gynostemma pentaphyllum* extract.

SUMMARY OF THE INVENTION

The present invention provides a composition for improving and treating metabolic syndrome, such as obesity, diabetes, or hyperlipidaemia, which includes a novel compound, that is, damulin A or damulin B, separated from a *Gynostemma pentaphyllum* extract.

Also, the present invention provides a novel *Gynostemma pentaphyllum* extract having an increased content of damulin A or damulin B, which shows an improving/treating effect on metabolic syndrome, such as obesity, diabetes, or hyperlipidaemia, and also provides a medicine, a health care food, or a functional food, which includes the same novel extract.

In the present invention, 2α,3β,12β-trihydroxydammar-20 (22)-E,24-diene-3-O-[β-D-glucopyranosyl-(1→)-β-D-glucopyranoside] named "damulin A" and 2α,3β,12β-trihydroxydammara-20,24-diene-3-O-[β-D-glucopyranosyl-(1→)-β-D-glucopyranoside] named "damulin B", which are novel dammarane-based saponins and have a capability for enzymatic activation of AMP-activated protein kinase (AMPK), are separated and analyzed from a *Gynostemma pentaphyllum* extract by using HPLC and NMR. The damulin A and the damulin B have the following structures.

*Gynostemma pentaphyllum* extract concentrate having increased contents of damulins (hereinafter, referred to as 'TG1022F').

In obtaining the novel *Gynostemma pentaphyllum* extract (TG1022F) having increased contents of damulins, it is required to maintain high temperature and high pressure. For this, a fermenter or an extractor, which is attached with a commercially available general high temperature•high pressure or high temperature/high pressure sterilizing device may be used.

The novel *Gynostemma pentaphyllum* extract may be generated in an ultra-high pressure state without a high tempera-

[Formula 1]

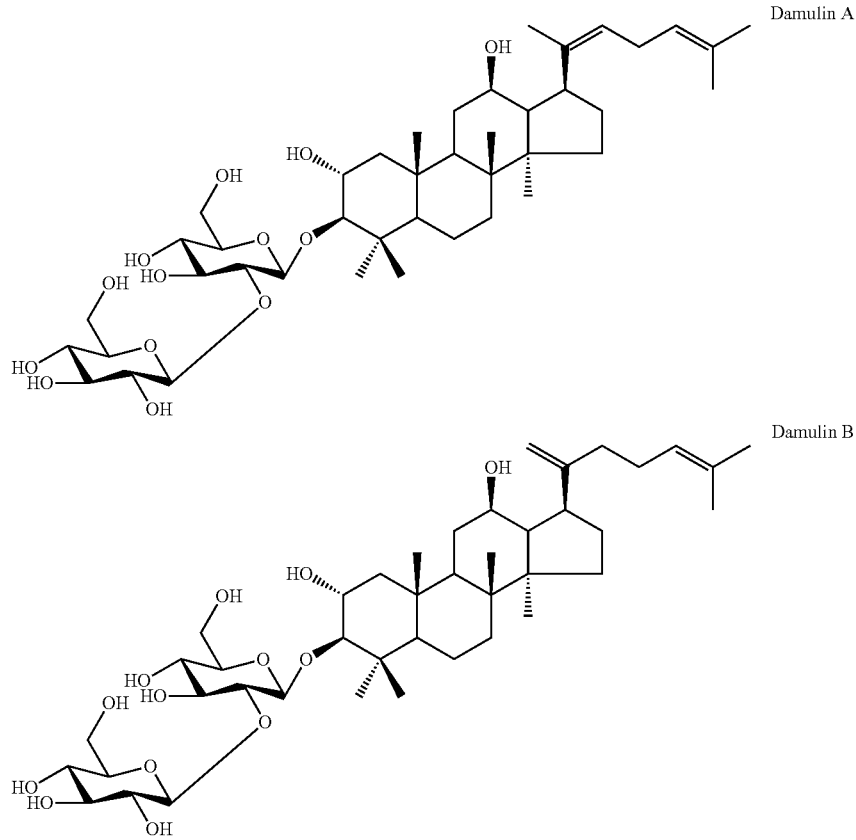

In order to separate damulins from a *Gynostemma pentaphyllum* extract, the *Gynostemma pentaphyllum* extract is prepared. First, dried *Gynostemma pentaphyllum* leaves are extracted with an ethanol aqueous solution having a volume 10 to 20 times as large as the volume of the leaves (preferably, a 20~80% ethanol aqueous solution), and a first supernatant is taken out. To the residual ethanol-dipped material of the *Gynostemma pentaphyllum* leaves, an ethanol aqueous solution (6 to 20 times) (preferably, a 20~80% ethanol aqueous solution) is again added, and then a second supernatant is taken out through 1~8 hour extraction at 65~95° C. Then, the first and second supernatants are put together and are filtrated by using gauze, and the solution obtained through the filtration is centrifuged (800~1,500×G) to remove floating matter. The resulting extracted product is concentrated to Brix concentration of 40 to 70 by vacuum-concentration to provide a *Gynostemma pentaphyllum* extract concentrate (hereinafter, referred to as 'TG1022"), and then the TG1022 is treated with high temperature and high pressure to provide a novel ture, and in order to maintain the ultra-high pressure state, a commercially available ultra-high pressure reactor may be used. For example, DFS-2L (Toyo Koatsu CO., Ltd. Japan) may be used. In preparing the novel *Gynostemma pentaphyllum* extract, the temperature preferably ranges from 40 to 125° C., and the pressure preferably ranges from 1.2 to 1100 atmospheres. The reaction time preferably ranges from 0.1 to 24 hours. In addition to the conditions of the high pressure and high temperature, in order to increase the contents of damulin A and damulin B in the *Gynostemma pentaphyllum* extract, a super high frequency range or oven may be used.

The separation and analysis of damulin A and damulin B may be carried out by the steps of: purifying a *Gynostemma pentaphyllum* extract through a column filled with an anion-exchange resin; washing the resulting product with purified water (5~15 times) washing the resulting product with 50% methanol (5~15 times); carrying out multi-step extraction by acetone (5~15 times), normal hexane (n-Hexane), ethyl acetate, and normal butanol (n-butanol); and separating damulin A and damulin B from a fraction having a high AMPK activity, from among extracts of the fractions, by using an HPLE method.

The novel *Gynostemma pentaphyllum* extract obtained by treating a *Gynostemma pentaphyllum* extract with high temperature and high pressure, according to the present invention, has increased contents of damulin A and damulin B, and thereby significantly improves a reducing effect on diabetes, obesity, body fat, blood neutral lipid, and cholesterol. In order to achieve a treating, improving, or preventing effect on such metabolic syndrome, active indicator ingredients, that is, damulin A and damulin B, are included in amounts of 0.5 to 10%, and 0.3 to 8%, and preferably in amounts of 0.7 to 7%, and 0.5 to 6%, respectively, with respect to the total dry weight of dried solids of the novel *Gynostemma pentaphyllum* extract with a novel composition according to the present invention.

A daily dosage of the novel *Gynostemma pentaphyllum* extract or its non-powdered liquid-state form (including damulin A and damulin B, in amounts of 0.5~10%, and 0.3~8%, respectively, in terms of solids) may be administered together with other additives or an excipient, and herein, the amount of the daily dosage is preferably 1 mg~100 g in terms of solids.

The formulation according to the present invention may be obtained in such a manner that the *Gynostemma pentaphyllum* extract containing damulin A or damulin B as an active ingredient is included in an amount of 0.01 to 100% with respect to the total composition.

Also, a food containing the composition according to the present invention may be used together with any kind of carrier within a composition range which does not reduce an anti-obesity effect, an anti-diabetic effect, and an anti-hyperlipidaemia effect. The composition according to the present invention may be added to thermal waters, filtrated water, distilled water, aerated water, juice, yogurt, milk, edible oil, food additives, ice cream, hamburger, cereal, cookie, bread, biscuit, processed meat, soymilk, sunsik (powdered food), nutrition adjuvant, processed fruit, fruit juice, etc., and the food containing the composition may include an extender, an antiseptic, a sweetening agent, a colorant, a humidity emulsifier, etc.

The administration method may be variously selected from acceptable methods, according to the clinical state of a disease. For example, oral or parenteral administration may be used. Examples of the parenteral administration include intravenous injection, intramuscular injection, subcutaneous injection, and intranasal administration that can have a solid, semi-solid, or liquid formulation. Besides, the composition may be administered by any form, such as suppository, cream, gel, patch, vaginal suppository, aerosol, etc. as long as the accurate amount of the composition can be administered. Also, in the pharmacologically composition, a conventional carrier or immuno-adjuvant is included. As the carrier that may be used in the present invention, any carrier may be used as long as it is pharmacologically acceptable. Also, as an excipient or a stabilizer, any kind of material may be used as long as it shows non-toxicity toward cells and mammals. A pharmacologically acceptable carrier may include a pH buffer solution, phosphoric acid, and citric acid, and also include ascorbic acid, etc. Also, as the carrier, water-soluble polymers, such as amino acids (e.g. polyvinyl pyrrolidone, glycine, glutamine, asparagine, arginine, lysine) and carbohydrate (e.g. glucose, mannose, dextrin) may be used. Also, as the carrier, chelate such as EDTA, mannitol, sorbitol, non-polar surfactant TWEEN, PEG (polyethylene glycol), and PLURONICS may be used. As the pharmacologically acceptable carriers and diluents, all kinds of solutions, dispersants, antibacterial and antifungal agents, isotonic agents, absorption delaying agents, and the like may be used. The method for using such agents for the pharmacological active ingredient is well known in the art. Any conventional agent may be included as long as it is compatible with the pharmacological active ingredient. In addition to the above described composition, complementary components may be added. Also, in the composition according to the present invention, chromium, manganese, zinc, niacin, vitamin B6, vitamin B12, etc. may be included. Furthermore, to the composition, HCA (hydroxycitric acid), CLA (conjugated linoleic acid), or the like, which is currently known to be effective in obesity, may be added.

For oral administration, pharmacologically acceptable non-toxic excipients may used together with the composition. Examples of the excipient include mannitol, polydextrose, maltodextrose, starch, lactose, stearic acid magnesium, saccharine, talc, cellulose, glucose, gelatin, sucrose, magnesium carbonate, etc. Such a composition may be used in the form of solution, suspension, tablets, pills, capsules, powder, and may be used together with pharmacologically acceptable non-toxic excipients.

Tablets, pills, and capsules may contain the following agents: a binder, such as tragacanth gum, acacia, corn starch or gelatin; excipients, such as calcium phosphate; a disintegrating agent, such as corn starch, potato starch, alginic acid, and the like; a lubricant, such as magnesium stearate; a sweetening agent, such as sucrose, or lactose; and a flavor extracted from peppermint, wintergreen, or cherry favoring. When the dosage unit form is a capsule, it may contain, in addition to materials of the above type, a liquid carrier. A syrup or elixir may contain, in addition to the active ingredients, sucrose as a sweetening agent, methyl or propylparabens as preservatives, and cherry or orange flavor as a colorant and a flavor. Any material used in preparing any dosage unit form should be pure and non-toxic. In the composition for such a formation, a diluent (such as lactose, sucrose, dicalcium phosphate) a lubricant (such as magnesium stearate) and a binder (such as starch, polyvinylpyrrolidone, acacia gum, gelatin, cellulose) may be included.

The novel *Gynostemma pentaphyllum* extract with increased contents of damulin A and damulin B has a significantly increased capability for phosphorylation and enzymatic activation of AMPK, compared to a conventional *Gynostemma pentaphyllum* extract.

The novel extract can significantly increase the phosphorylation of ACC (acetyl-CoA carboxylase) which is a subordinate target protein of AMPK and a main enzyme in biosynthesis of fatty acid, resulting in more significant reduction of enzymatic activity of ACC. In other words, a novel *Gynostemma pentaphyllum* extract with increased contents of damulin (TG1022F) is more effective in inhibiting body fat synthesis, accelerating β-oxidation of fatty acid, inhibiting cholesterol biosynthesis, treating/improving hyperlipidaemia, and treating/improving obesity, compared to a conventional *Gynostemma pentaphyllum* extract (TG1022) with non-increased damulin contents. Also, compared to TG1022, TG1022F can more efficiently reduce blood glucose of a diabetic patient by non-insulin dependently significantly increasing the movement of GLUT4 (for transporting glucose into cells) toward a cell membrane.

As a result, it can be said that the novel Gynostemma pentaphyllum extract with increased contents of damulin A and damulin B, prepared by the method of the present invention, is more effective in improving or treating metabolic syndrome, such as obesity, diabetes, or hyperlipidaemia, compared to a conventional *Gynostemma pentaphyllum* extract.

BRIEF DESCRIPTION OF THE DRAWINGS

The above and other objects, features and advantages of the present invention will be more apparent from the following detailed description taken in conjunction with the accompanying drawings, in which:

FIG. 7 shows phosphorylation increases of the enzyme protein of AMPK and ACC with respect to concentrations, by a dried product a novel *Gynostemma pentaphyllum* extract (TG1022F) with a novel composition whose contents of damulin A and damulin B were increased up to 0.89% and 0.68%;

FIG. 8 shows a change in the phosphorylation increase of AMPK and ACC in soleus muscle of obese mice, according to the administration of a dried product a novel *Gynostemma pentaphyllum* extract (TG1022F) with a novel composition whose contents of damulin A and damulin B were increased up to 0.89% and 0.68%.

DETAILED DESCRIPTION OF THE EXEMPLARY EMBODIMENTS

Figure 1:
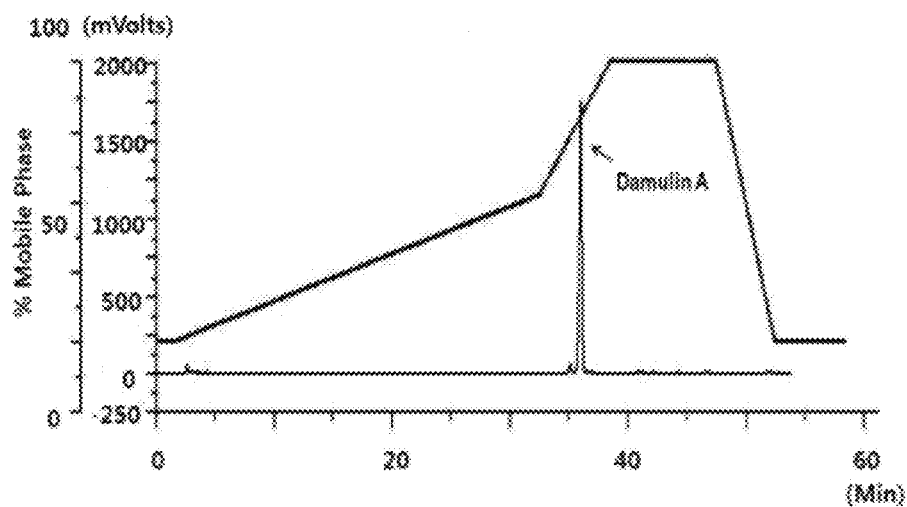
FIGS. 1 and 2 show analysis results of HPLC spectrum of damulin A and damulin B separated/purified as novel dammarane-type saponins that are active ingredients for increasing AMPK activity.

Hereinafter, the present invention will be described in detail with reference to Examples. However, the following examples are illustrative only, and the scope of the present invention is not limited thereto.

EXAMPLE 1

Separation of Damulin as an AMPK Activating Material, from a *Gynostemma pentaphyllum* Extract 5 kg of dried *Gynostemma pentaphyllum* leaves was dipped in 50 l of 50% ethanol, and then, after first extraction at 90° C. for 6 hours, a first supernatant was collected. To the residual ethanol-dipped material of the *Gynostemma pentaphyllum* leaves, 50 l of 50% ethanol was again added, and then a second supernatant was collected through 6 hour extraction at 90° C. The first and second supernatants were put together and were filtrated by using gauze, and the solution obtained through the filtration was centrifuged (1,000×G) to remove floating matter. The resulting extracted product was concentrated to Brix concentration of 50 by vacuum-concentration, and then the resulting concentrated product was used to separate damulin (an AMPK activating material).

In order to separate pure damulin, the 50-Brix concentrated *Gynostemma pentaphyllum* extract was purified through a column (20×65 cm) filled with an HP-20 anion-exchange resin (Mitsubishi Chemical Corporation); the resulting product was firstly washed with 10 l of water, and then washed with 10 l of 50% methanol; and a acetone fraction was obtained and concentrated via 10 l of acetone. Then, the resulting concentrate was suspended by mixing with 1.5 l of water, and then a hexane layer (200 g) was obtained by three successive extraction steps with 1.5 l of normal hexane (n-Hexane), an ethyl acetate layer (200 g) was obtained by three successive extraction steps with 1.5 l of ethyl acetate, and a butanol layer (200 g) was obtained by three successive extraction steps with 1.5 l of normal butanol (n-butanol).

A butanol layer (100 g), from among the layers, which has the highest activating capability for AMPK phosphorylation increase in L6 myotube cells, was chromatographed on a silica gel (Merck) column (15×65 cm; particle size: 63-200 μm) with a concentration gradient of chloroform:methanol:water=5:1:0.1 (initial solvent mixed ratio) to chloroform:methanol:water=0:1:0.1 (final solvent mixed ratio), and thereby active ingredients were separated and a total of 5 fractions (B.1-B.5) were obtained.

The fractions were analyzed by HPLC, and as a result, it was determined that B.3 and B.4 contain very similar ingredients. Thus, the two fractions were put together to newly provide B34 fraction. They were chromatographed on an ODS-A silica gel (Merck) column (6.5×65 cm; particle size: 12 nm-150 μm) by a multi-step concentration gradient of 1:1 (initial step) to 0:1 (final step) in a mixed ratio of water to methanol (as a mixed solvent for ingredient separation), and thereby 6 fractions (B.34-1 to B.34-6) were obtained.

A B34-5 fraction, from among the fractions, which has the highest activating capability for AMPK phosphorylation increase in L6 cells, was subjected to HPLC analysis and UV measuring device (205 mm) measurement, and then active ingredients were again separated. For this, a semi-preparative column (RP-C18 Package column, 10×250 mm, 10 particle size; RS Tech, Korea) was used, and the flow rate of the test sample was 2 ml per minute. As a solvent, at the initial step, 75% methanol containing 0.1% formic acid was used to carry out 75-minute separation, and then 100% methanol was used to carry out 15-minute separation. As a result, 14 mg of damulin A and 10 mg of damulin B were separated, respectively.

Figure 2:
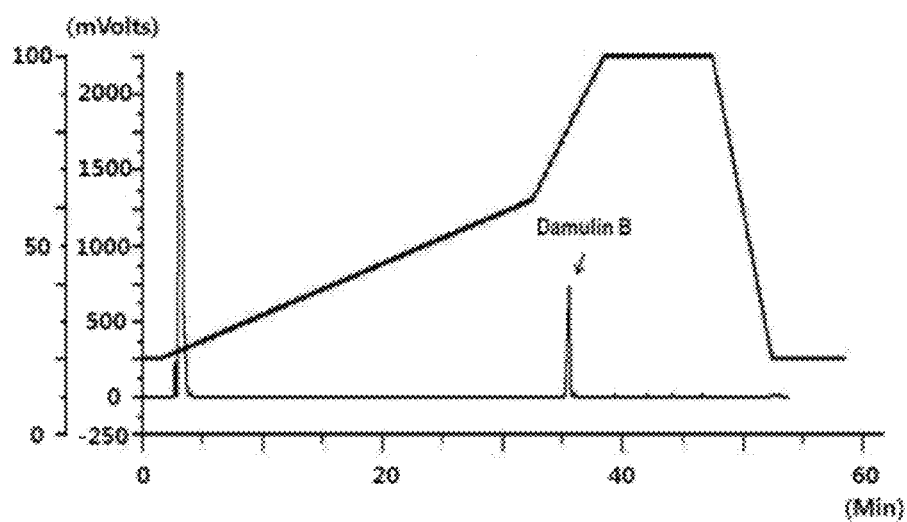

In order to determine the purified extent of the separated damulin A and damulin B, an HPLC analysis was carried out [apparatus: Gilson 321Pump/GX271 liquid handler, detector: UV/VIS 155 Detector (205 nm), column: Optimapak C18 (250×4.6 mm, RS tech), flow rate: 0.8 mL/min, solvent: A-H2O/B-MeCN, solvent concentration gradient: B 20% (0-2 minutes)/20-62% (2-33 minutes)/62-100% (33-39 minutes)/100% (39-48 minutes)/100-20% (48-53 minutes)/20% (53-60 minutes)]. For this, damulin A was dissolved in methanol at a concentration of 8 mg/ml, and then 20 μl of a test sample was subjected to an absorbance analysis by a analysis column and a UV measuring device (205 mm) under the proper HPLC analysis conditions. Damulin B was dissolved in methanol containing 5% DMSO, at a concentration of 4 mg/ml, and then 20 μl of a test sample was subjected to an analysis under the same conditions as damulin A. As a result, as shown in FIGS. 1 and 2, it was determined that each of the separated and purified damulin A and damulin B has a spectrum showing a single peak, and has a purity of at least 97% or more.

EXAMPLE 2

Structure Determination of Separated and Purified Damulin

In order to determine the structure of damulin as a compound, [M+Na]$^+$ peak was observed at 805.4717 (cacld. 805.4714) through FAB Mass analysis. $^1$H NMR, $^{13}$C NMR and HMBC (heteronuclear multiple-bonding correlation) spectrums were measured to determine the structure of the separated/purified material.

In the $^1$H-NMR spectrum, 7 angular methyl groups show single peaks, and in $^{13}$C-NMR, characteristic carbon peaks having a double bond were shown at δC 124.4, 124.7, 132.3, 140.5 ppm. Also, from proton peaks at 5.08 and 5.26 ppm, it was determined that two glucoses are bonded in the compound. From proton peaks shown at δH 3.02, 3.63, 3.75 ppm and carbon peaks shown at δC 68.3, 74.1, and 96.8 ppm in $^1$H-NMR spectrum data, it was found that 3 hydroxyl groups were substituted. Also, from the proton coupling constants of Nos. 2 and 3, it was found that two hydroxyl groups exist as 2α, and 3β diequatorial types. Through the comparison of various kinds of physical/chemical properties and $^{13}C$ NMR data with other references, damulin was identified to be a novel compound. In order to determine the structure of the compound, HMBC spectrum was measured. As a result, from the connection point between peaks from $^1H$ to $^{13}C$ NMR, it was found that two glucoses are bonded at position 3 in the compound. Then, through the determination of $^1H$ and $^{13}C$ NMR structures at each position, the compound was determined as a novel compound, 2α,3β,12β-trihydroxydammar-20(22)-E,24-diene-3-O-[β-D-glucopyranosyl-(1→)-β-D-glucopyranoside], and was named 'damulin A'.

Damulin B is amorphous powder, and was measured as m/z 783.4905 ([M+H]$^+$ calcd. 783.4895) by $^{13}C$ NMR and HR-ESI-MS. Its molecular formula was identified as $C_{42}H_{70}O_{13}$. Through the comparison of $^1H$ and $^{13}C$ NMR spectrums of compound 2 with damulin A, it was determined that the two compounds have the same aglycone moiety. A main difference between damulin A and damulin B is that a tertiary $CH_3$ group in aglycone of damulin A is substituted with a terminal $CH_2$ group of damulin B. Also, a double bond of olefinic methine group of C-22 is substituted with quaternary carbon of C-20 (δC 140.5). In the $^1H$ NMR spectrum, instead of the methyl signal (δ 1.63, 3H, s) of damulin A, two wide single peaks (δ 4.69 and 4.88, each 1H, br, s) of damulin B are shown. Also, a typical olefinic proton signal which is not shown in damulin A is shown at δ 5.26 (1H, br, t like, J=6.9 Hz).

From the comparison of the $^{13}C$ NMR spectrums of damulin B and damulin A with each other, it can be seen that the olefinic carbon signal (δC 124.7, C-22) and the methyl signal (δC 13.1, C-21) of damulin A are substituted with the methylene signal (δC 35.1), and the terminal methylene peak (δC 108.7) of damulin B, respectively. Another difference between them is that the chemical shift of the quaternary carbon (δC 140.5, C-20) in damulin A was moved to a low magnetic field (δC 156.3) in damulin B. Also, in the hydrolysis of damulin B, D-Glucose is generated. Based on the $^1H$ and $^{13}C$ NMR data (Table 1), and the two-dimensional NMR data (Table 1), such as $^1H$-$^1H$ COSY, gHSQC, and $^1H$-$^{13}C$ HMBC spectroscopic data, two glucoses of damulin B were identified. Through the comparison of the chemical shift and the coupling constant in $^1H$, and $^{13}C$ NMR spectrums of damulin A with those of damulin B, it is found that damulin B also has two glucosyl units of β-configuration type. Anomeric protons, at δ 4.45 (1H, d, J=8.0 Hz, H-1' of glc'); δC 105.0 (C-1' of glc'), and δ 4.75 (1H, d, J=8.0 Hz, H-1" of glc"); δC 104.5 (C-1" of glc"), support this conclusion. The linkage portion between two glucoses and aglycone was determined by the HMBC result (Table 1). Based on the above result, the structure of damulin B was identified as 3-O-[β-D-glucopyranosyl-(1→)-β-D-glucopyranosyl]-2α,3β,12β-trihydroxy-dammara-20,24-diene. Table 1 shows the results of $^1H$ (500 MHz) and $^{13}C$ (100 MHz) NMR for structural analysis of damulin A and damulin B, on $CD_3OD$.

TABLE 1

| position | damulin A $\delta_C$ | damulin A $\delta_H$ (J in Hz) | damulin B $\delta_C$ | damulin B $\delta_H$ (J in Hz) |
|---|---|---|---|---|
| 1 | 48.1 | 0.92, m 2.10, dd (5.4, 13.2) | 48.1 | 0.94, m 2.11, m |
| 2 | 68.3 | 3.75, m | 68.3 | 3.75, m |
| 3 | 96.8 | 3.02, d (9.3) | 96.8 | 3.01, d (9.5) |
| 4 | 42 | — | 42 | — |
| 5 | 57.4 | 0.89, m | 57.4 | 0.88, m |
| 6 | 19.4 | 1.54, m 1.59, m | 19.4 | 1.53, m 1.59, m |
| 7 | 36.1 | 1.35, m 1.58, m | 36.1 | 1.35, m 1.58, m |
| 8 | 41.3 | — | 41.3 | — |
| 9 | 51.9 | 1.52, m | 52 | 1.52, m |
| 10 | 39.1 | | 39.1 | |
| 11 | 32.7 | 1.28, m 1.82, m | 33.1 | 1.28, m 1.81, m |
| 12 | 74.1 | 3.63, m | 73.9 | 3.59, m |
| 13 | 51.5 | 1.80, m | 53 | 1.85, m |
| 14 | 52.1 | — | 52.3 | — |
| 15 | 33.5 | 1.11, m 1.69, m | 33.3 | 1.11, m 1.70, m |
| 16 | 29.6 | 1.44, m 1.89, m | 31.8 | 1.42, m 2.00, m |
| 17 | 51.4 | 2.59, m | 49.6 | 2.58, m |
| 18 | 16.3 | 1.05, s | 16.3 | 1.06, s |
| 19 | 18.1 | 0.99, s | 18.1 | 0.99, s |
| 20 | 140.5 | — | 156.3 | — |
| 21 | 13.1 | 1.63, s | 108.7 | 4.69, br, s 4.88, br, s |
| 22 | 124.7 | 5.26, t (6.9) | 35.1 | 2.02, m 2.15, m |
| 23 | 28.1 | 1.68, m 2.67, m | 27.8 | 2.22, m 2.14, m |
| 24 | 124.4 | 5.08, t (7.2) | 125.9 | 5.17, m |
| 25 | 132.2 | — | 132.2 | — |
| 26 | 26 | 1.67, s | 26 | 1.69, s |
| 27 | 17.9 | 1.61, s | 17.9 | 1.63, s |
| 28 | 17.3 | 0.93, s | 17.3 | 0.93, s |
| 29 | 28.8 | 1.14, s | 28.8 | 1.13, s |
| 30 | 18.1 | 0.92, s | 18 | 0.91, s |
| Glu | | | | |
| 1 | 105 | 4.45, d (7.5) | 105 | 4.45, d (8.0) |
| 2 | 80.7 | 3.69, m | 80.7 | 3.69, m |
| 3 | 78.8 | 3.59, m | 78.8 | 3.60, m |
| 4 | 71.4 | 3.37, m | 71.3 | 3.36, m |
| 5 | 78.2 | 3.20, m | 78.2 | 3.22, m |
| 6 | 62.5 | 3.66, m 3.87, br, d (18.5) | 62.5 | 3.62, m 3.84, br, d (12.0) |
| Glu/Xyl | | | | |
| 1 | 104.5 | 4.75, d (7.5) | 104.5 | 4.75, d (8.0) |
| 2 | 76.3 | 3.24, m | 76.3 | 3.24, m |
| 3 | 78.4 | 3.25, m | 78.4 | 3.26, m |
| 4 | 72.2 | 3.19, m | 72.2 | 3.21, m |
| 5 | 78.1 | 3.36, m | 78 | 3.36, m |
| 6 | 63.4 | 3.62, m 3.84, br, d (10.2) | 63.3 | 3.66, m 3.87, dd (2.5, 12.0) |

EXAMPLE 3

Phosphorylation Increasing Effect on AMPK and ACC by Damulin A and Damulin B

Phosphorylated activated AMPK increases the phosphorylation of ACC and HMG-CoA reductase, resulting in the reduction of the activity of ACC and HMG-CoA reductase (Henin, 1995). Accordingly, the phosphorylation of AMPK inhibits the biosynthesis of fatty acid, increases β-oxidation in mitochondria, and reduces the synthesis of fat and cholesterol in the liver tissue. The activity of AMPK may be determined by determining whether or not the phosphorylation of a threonine amino acid residue at position 172 was increased.

ACC is an important enzyme for regulating lipid metabolism in liver and muscle tissues. This enzyme carboxylates acetyl-CoA to produce malonyl-CoA. Malonyl-CoA is the most important factor for regulating β-oxidation of fatty acid within mitochondria. When the concentration of malonyl-CoA increases, the activity of CPT-1 (carnitine palmitoyl-CoA transferase) in mitochondrial membrane is reduced, thereby inhibiting β-oxidation of fatty acid, and on the other hand, when the concentration of malonyl-CoA decreases, β-oxidation is increased, accelerating the reduction of body fat. ACC is a subordinate target protein in AMPK activity, and is phosphorylated by the activation of AMPK. Accordingly, the AMPK activation accelerates the enzymatic inactivation of ACC. This reduces the concentration of malonyl-CoA, and thereby the activity of CPT-1 in mitochondrial membrane is increased, thereby increasing β-oxidation of fatty acid.

Figure 3:
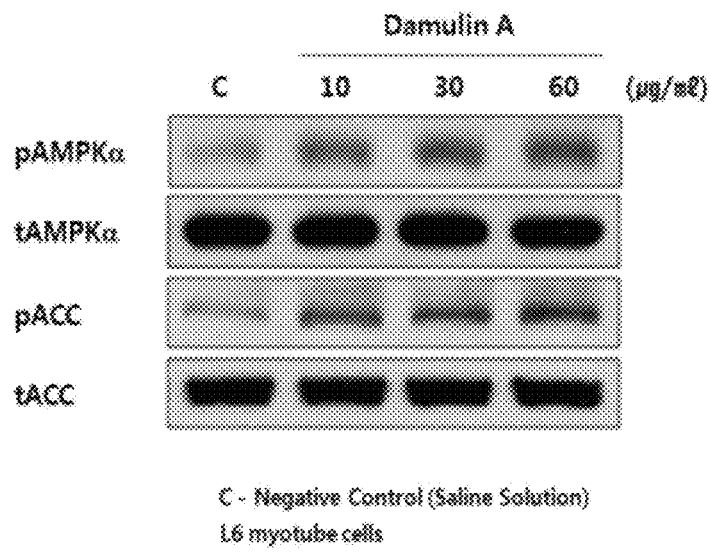
FIGS. 3 and 4 are photos showing phosphorylation increases of AMPK(A) and ACC(B) with respect to compound concentrations in L6 myotube cells, by separated/purified damulin A and damulin B.
Figure 4:
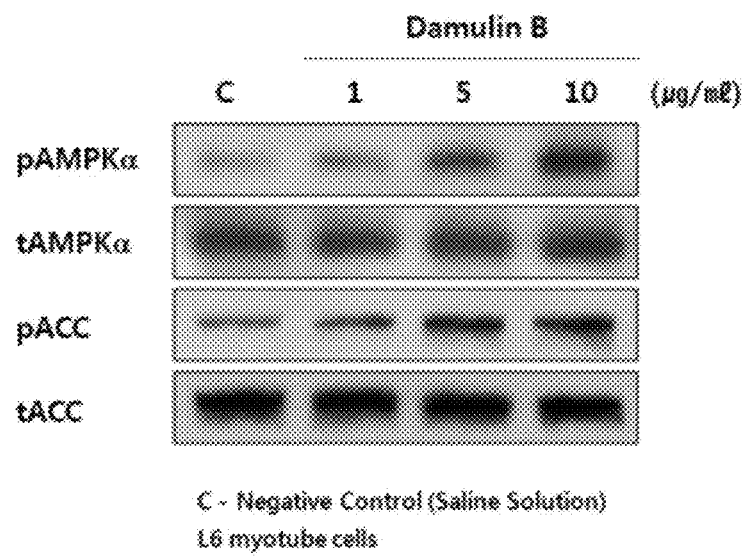

Accordingly, differentiated L6 myotube cells were treated with individually separated damulin A with different concentrations (10, 30, and 60 μg/ml), and treated with individually separated damulin B with different concentrations (1, 5, and 10 μg/ml), for 2 hours. The increased extent of the phosphorylation of a threonine residue at (Thr)-172 of AMPK α subunit, and a serine residue at Ser-79 of an ACC enzyme protein was analyzed through western blot analysis according to the method of Hwang, et al. (Biochem. Biophys. Res. Commun. 371, 289-293, 2008). As a result, it was determined that the treatment with damulin A and damulin B concentration-dependently increased the phosphorylation of AMPK and ACC within L6 myotube cells, compared to a control group (see FIGS. 3 and 4). Also, both damulin A and damulin B were determined to be active ingredients which phosphorylate and activate AMPK, and phosphorylate and inactivate ACC.

EXAMPLE 4

Fat Reducing Effect Through β-Oxidation Acceleration of Fatty Acid by Damulin A and Damulin B When AMPK is activated, the activity of ACC is reduced, thereby reducing the concentration of malonyl-CoA within mitochondria. This accelerates the transport of fatty acid into mitochondria, and thereby increases β-oxidation. Thus, due to the reduction of body fat, an obesity inhibiting effect can be achieved. Cultured L6 myotube cells were treated with purely separated damulin A and damulin B, and the improving effect on β-oxidation of fatty acid was analyzed by the method of Hwang, et al. (Biochem. Biophys. Res. Commun. 377, 1253-1258).

Figure 5:
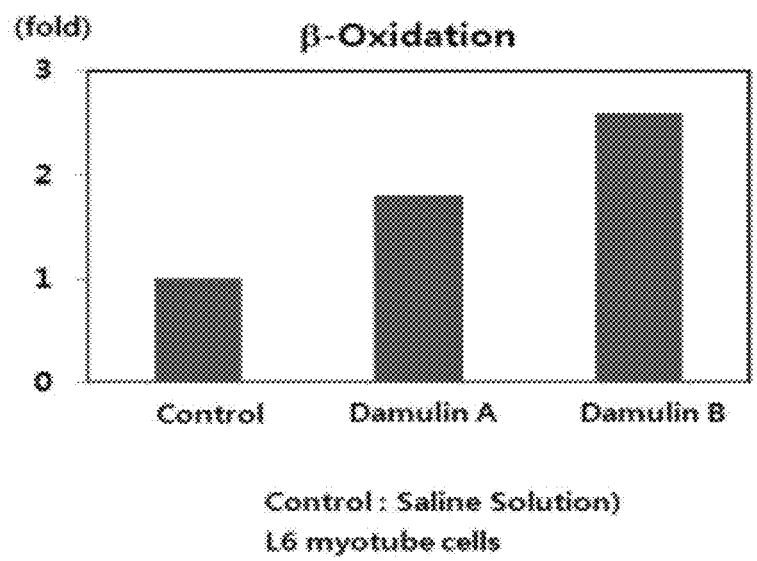
FIG. 5 shows an increasing effect on β-oxidation of fatty acid, by damulin A and damulin B.

As a result, it was observed that damulin A (30 μg/ml) and damulin B (5 μg/ml) increased β-oxidation of fatty acid 1.8 times and 2.6 times (see FIG. 5). Therefore, based on the result, damulin A and damulin B are determined to be materials which are highly effective in inhibiting or treating obesity by accelerating the reduction of body fat.

EXAMPLE 5

Accelerating Effect of Glucose Absorption into Cells Damulin A and Damulin B

It is well known that the activation of AMPK also increases the glucose absorption into cells, and thus causes a blood glucose level reducing effect (Hardie, et al., FEBS Lett. 546, 113-120, 2003; Carling, et al., Trends. Biochem. Sci. 29, 18-24, 2004; Kahn, et al., Cell Metab. 1, 15-25, 2005; Cool, et al., Cell Metab. 3, 403-416, 2006; Lee et al., Diabetes, 55, 2256-2264, 2006; Hwang et al., Biochem. Biophys. Res. Commun. 371, 289-293, 2008). Accordingly, the treatment of damulin A and damulin B on L6 myotube cells was carried out to determine the influence on the glucose absorption into cells.

Figure 6:
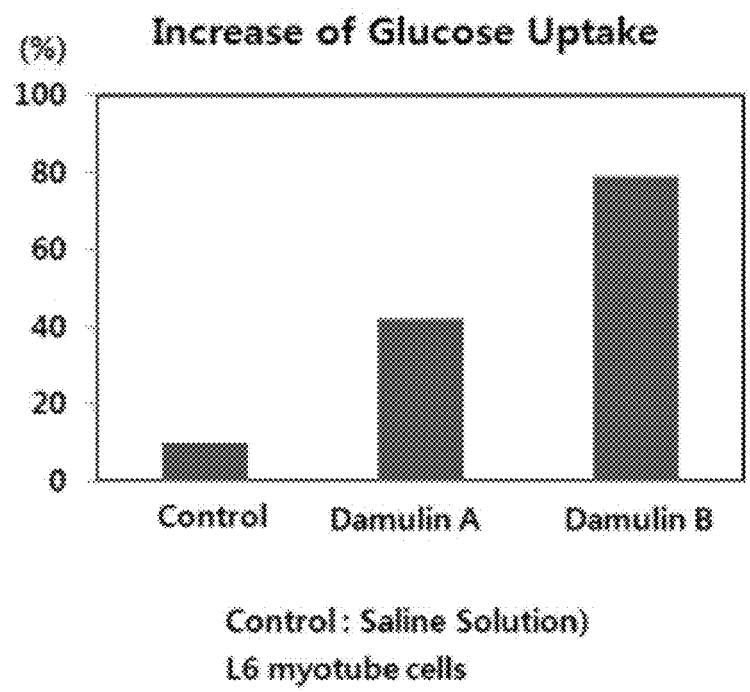
FIG. 6 shows an increasing effect on glucose absorption into cells, by damulin A and damulin B.
Figure 9:
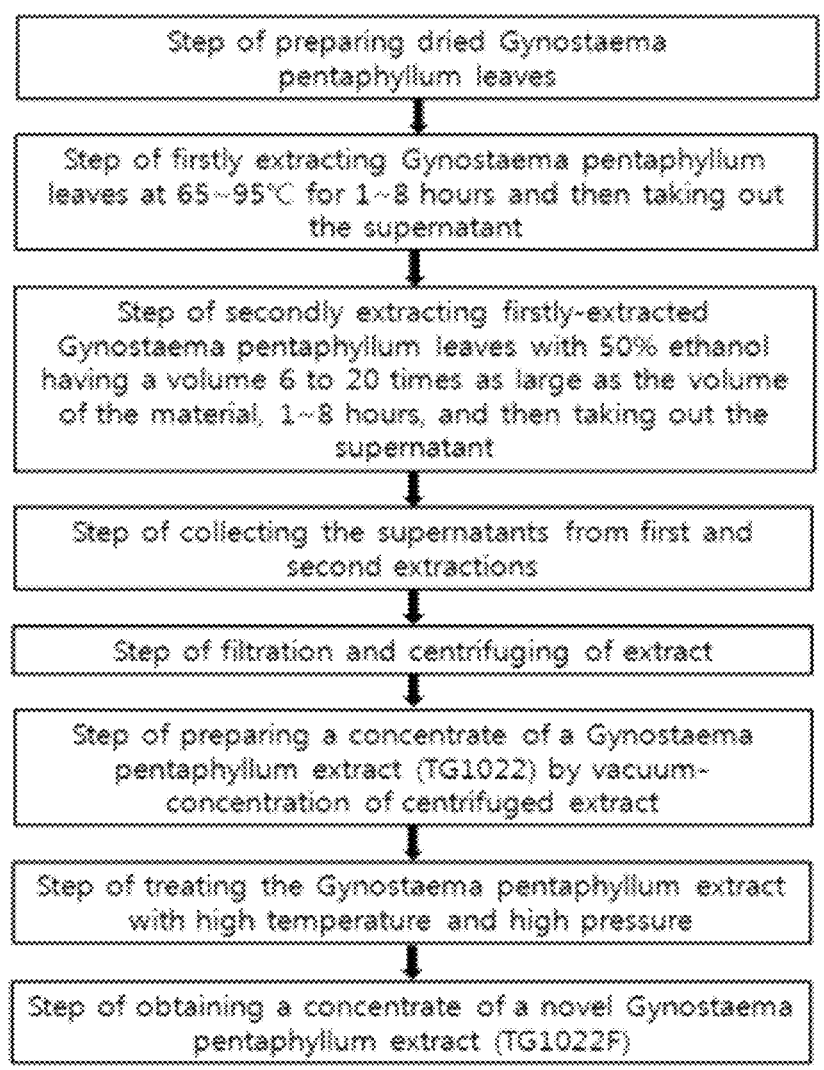
FIG. 9 shows a method of preparing a *Gynostemma pentaphyllum* extract, and a novel *Gynostemma pentaphyllum* extract with increased contents of damulin A and damulin B.

To cultured L6 myotube cells, high concentration glucose was added together with 2-DG (2-deoxy-[3H]D-glucose) (a radioactive isotope that is not decomposed within a cell) according to the method of Hwang et al. (Biochem. Biophys. Res. Commun. 377, 1253-1258), and then the accelerated extent of 2-DG absorption into cells by damulin A (30 μg/ml) and damulin B (5 μg/ml) was analyzed. As a result, in the damulin A-treated cells, the capability of absorbing glucose was increased by 42% on the average, and in the damulin B-treated cells, the capability was increased by about 79% (see FIG. 6). Therefore, based on the result, both damulin A and damulin B are determined to have a high anti-diabetes effect by decreasing blood glucose level.

EXAMPLE 6

Preparation of *Gynostemma pentaphyllum* Extract Having Increased Damulin Contents Through Treatment of High Temperature and High Pressure As can be seen in the above Examples 4 and 5, novel compounds, that is, damulin A and damulin B, were found to be active ingredients which activate AMPK and thereby deactivate ACC. However, a conventional *Gynostemma pentaphyllum* extract (TG1022) contains damulin A and damulin B in amounts not sufficient to show a valid effect. Accordingly, a novel *Gynostemma pentaphyllum* extract (TG1022F) with a novel composition having increased contents of damulin A and damulin B was prepared, and then it was found that the novel *Gynostemma pentaphyllum* extract (TG1022F) has a strong AMPK activating capability.

The concentrate of the novel *Gynostemma pentaphyllum* extract (TG1022F) was prepared by performing a high temperature/high pressure reaction or a ultra-high pressure reaction on the conventional *Gynostemma pentaphyllum* extract (TG1022) obtained by ethanol extraction at room temperature and atmospheric pressure.

In the high temperature/high pressure reaction, a conventional high temperature/high pressure sterilizer (autoclave) or a ultra-high pressure reactor (DFS-2L, Toyo Koatsu CO., Ltd. Japan) was used to maintain the high temperature/high pressure state of the concentrate of simple extract of *Gynostemma pentaphyllum* (30 ml).

The contents of damulin A and damulin B within the dried product obtained by drying the concentrate of the novel *Gynostemma pentaphyllum* extract (TG1022F) were analyzed by using HPLC. Herein, as shown in FIG. 1, a quantitative standard curve was made with respect to concentrations by using the separated damulin A damulin B having purity as standards, and the contents were calculated from respective peak area ratios of the test samples. As a result, under the conditions of varying high temperatures, high pressures, or times, in the concentrate of the novel *Gynostemma pentaphyllum* extract (TG1022F), the contents of damulin A damulin B increased in proportion to temperature, pressure, time, etc. (Table 2). Accordingly, in the present invention, when the concentrate of the *Gynostemma pentaphyllum* extract is processed with a processing condition including both high temperature and high pressure, it is possible to prepare the concentrate of the novel *Gynostemma pentaphyllum* extract (TG1022F) having significantly increased contents of damulin A and damulin B, in proportion to the processing time. Table 2 shows the increase of damulin content included in a *Gynostemma pentaphyllum* extract under the condition of high temperature and high pressure.

TABLE 2

| Reaction conditions | | | Content of damulins % (w/w) | |
|---|---|---|---|---|
| temperature (° C.) | Time (Hour) | Pressure (atmosphere) | damulin A | damulin B |
| Control group (TG1022) | | | 0.37 ± 0.03 | 0.28 ± 0.02 |
| 121 | 0.5 | 1.2 | 0.70 ± 0.04 | 0.56 ± 0.04 |
| | 1 | | 0.89 ± 0.07 | 0.68 ± 0.04 |
| | 2 | | 1.53 ± 0.06 | 1.16 ± 0.07 |
| | 3 | | 2.01 ± 0.08 | 1.47 ± 0.08 |
| | 4 | | 2.49 ± 0.09 | 1.81 ± 0.10 |
| | 8 | | 3.21 ± 0.03 | 2.42 ± 0.03 |
| | 12 | | 4.51 ± 0.03 | 4.12 ± 0.02 |
| | 24 | | 6.82 ± 0.06 | 5.54 ± 0.05 |
| 45 | 12 | 297 | 0.62 ± 0.03 | 0.52 ± 0.02 |
| | | 691 | 0.83 ± 0.07 | 0.74 ± 0.07 |
| | | 1087 | 1.21 ± 0.06 | 1.13 ± 0.06 |
| | 24 | 297 | 0.82 ± 0.02 | 0.71 ± 0.05 |
| | | 691 | 1.22 ± 0.04 | 0.97 ± 0.03 |
| | | 1087 | 1.81 ± 0.06 | 1.33 ± 0.02 |

EXAMPLE 7

Phosphorylation Increasing Effect on AMPK and ACC by a Novel *Gynostemma pentaphyllum* Extract Having Increased Damulin Contents On the novel composition-containing *Gynostemma pentaphyllum* extract (TG1022F) prepared according to the method of Example 6, whose contents of damulin A and damulin B were increased up to 0.89% and 0.68%, respectively, the concentration dependence in the activation increasing capability of an AMPK signaling system was analyzed by using L6 myotube cells. As a result, as shown in FIG. 7, a simple *Gynostemma pentaphyllum* extract, that is, TG1022, even when treated with a concentration of 120 μg/ml, cannot cause the phosphorylation of AMPK and ACC at all, which is similar to a non-treated control group. However, TG1022F which is prepared in such a manner that the contents of damulin A and damulin B were increased up to 0.89% and 0.68%, respectively, significantly accelerated the phosphorylation of AMPK and ACC even at a treatment concentration of 60 μg/ml, and also concentration-dependently increased the phosphorylation of AMPK and ACC when the treatment concentration was increased up to 90 μg/ml and 120 μg/ml. Especially, when TG1022 (the simple *Gynostemma pentaphyllum* extract concentrate which was not treated with high temperature/high pressure, damulin A content: 0.37%, damulin B content: 0.28%), and TG1022F (which was treated with high temperature/high pressure under the reaction conditions of 121° C., 1.2 atmospheres, 1 hour) (damulin A content: 0.89%, damulin B content: 0.68%) were treated with the same concentration, it was determined that TG1022F with increased damulin contents has a much better phosphorylation capability on AMPK and ACC than TG1022 with non-increased damulin contents through the comparison of their effects with each other.

EXAMPLE 8

Weight Loss Effect in an Obese Animal Model by a Novel *Gynostemma pentaphyllum* Extract Ob/ob mice with leptin gene mutation, used as an obese, hyperglycemic, insulin resistant animal model were used to analyze an anti-obesity effect of a *Gynostemma pentaphyllum* extract with increased damulin contents. For this, to the mice, the novel *Gynostemma pentaphyllum* extract (TG1022F) prepared according to the method of Example 6, whose contents of damulin A and damulin B were increased up to 0.89% and 0.68%, respectively, was orally administered in doses of 150 mg/kg and 300 mg/kg, respectively, daily for 8 weeks. Herein, to a control group, saline solution was administered. Also, the administration of TG1022F was compared to that (300 mg/kg) of TG1022 (a simple *Gynostemma pentaphyllum* extract).

Herein, 8 male animals were used for each administration group. As a result, as noted in Table 5, the group to which TG1022F (damulin A content: 0.89%, damulin B content: 0.68%) was daily administered in doses of 150 mg/kg and 300 mg/kg showed weight loss by 2.95 g and 4.58 g compared to the saline solution control group, after 8 weeks (see Table 3). However, herein, the group to which TG1022 was administered in a dose of 300 mg/kg did not show a significant weight change, compared to the saline solution control group. Meanwhile, there was no change in food intake in all administration groups. Therefore, it was determined that the weight loss effect by TG1022F with increased contents of damulin A and damulin B was not caused by the reduction of food intake (see Table 3).

Table 3 shows a weight loss effect by administration of TG1022F (a novel *Gynostemma pentaphyllum* extract with a novel composition having increased contents of damulin A and damulin B (damulin A content: 0.89%, damulin B content: 0.68%) in obese mice (ob/ob)

TABLE 3

| Extract taken in by animal group | Weight loss compared to control group (g) | Food intake (g/day) |
|---|---|---|
| TG1022 (300 mg/kg) (simple Gynostemma pentaphyllum extract) | 1.04 g | 5.21 ± 0.451 |
| TG1022F (150 mg/kg) (novel Gynostemma pentaphyllum extract) | 2.54 g | 5.36 ± 0.45 |
| TG1022F (300 mg/kg) (novel Gynostemma pentaphyllum extract) | 4.58 g | 5.29 ± 0.52 |

EXAMPLE 9

Phosphorylation Increasing Effect on AMPK and ACC in Animal Muscle by a Novel *Gynostemma pentaphyllum* Extract In order to determine whether or not the weight loss effect obtained from Example 8 was caused by the phosphorylation increase of AMPK and ACC, soleus muscle was separated from the mice administered with TG1022F (an extract whose contents of damulin A and damulin B were increased up to 0.89%, and 0.68%), and the phosphorylation extent of AMPK and ACC was analyzed by western blot analysis. As a result, as shown in FIG. 8, it was determined that the group administered with TG1022F having increased contents of damulin A and damulin B shows a more significant phosphorylation increase of AMPK and ACC, compared to the saline solution control group and the group administered with TG1022 (a simple *Gynostemma pentaphyllum* extract). Based on the result, it was determined again that the weight loss effect by TG1022F with increased damulin contents in Example 8 was caused by TG1022F. In other words, TG1022F caused the activation of AMPK in animal muscle and thereby efficiently caused the inactivation of ACC.

EXAMPLE 10

Weight/Waist-Circumference Loss Effect in a Human Body by a Novel *Gynostemma pentaphyllum* Extract To adult males and females (aged between 21 to 71), TG1022 (a simple *Gynostemma pentaphyllum* extract), and TG1022F (whose contents of damulin A and damulin B were increased up to 0.89%, and 0.68%, respectively) were orally administered in a dose of 300 mg/kg, daily for 12 weeks. Herein, TG1022 was orally administered to 10 males and 10 females, and also TG1022F was orally administered to 10 males and 10 females. The weight was measured by a scale, and the waist circumference was measured with respect to a middle portion between the bottom of the 10$^{th}$ rib and the iliac crest.

As a result, as noted in Table 4, in the group administered with TG1022F having increased damulin contents, both the male group and the female group showed weight loss by 4.3 kg and 2.1 kg on the average, and waist circumference loss by 5.4 cm and 5.8 cm on the average, respectively. Meanwhile, in the group administered with TG1022, the male group and the female group showed weight loss by 0.6 kg and 0.4 kg on the average, and waist circumference loss by 0.7 cm and 0.8 cm on the average, respectively (see Table 7). Based on the result, the novel composition-containing TG1022F with increased contents of damulin A and damulin B was determined to have a much better weight/body fat reducing effect, compared to TG1022 (a simple *Gynostemma pentaphyllum* extract). Table 4 shows a weight/waist-circumference loss effect in a human body by TG1022F (a novel *Gynostemma pentaphyllum* extract having increased contents of damulin A and damulin B).

TABLE 4

| Experimental group for human body | | Weight loss (kg) | Waist circumference loss (cm) |
| --- | --- | --- | --- |
| TG1022 (simple Gynostemma pentaphyllum extract) | Male Female | 0.6 ± 0.10 0.4 ± 0.07 | 0.7 ± 0.21 0.8 ± 0.15 |
| TG1022F (novel Gynostemma pentaphyllum extract) | Male female | 4.3 ± 0.27 2.1 ± 0.15 | 5.4 ± 0.27 5.8 ± 0.33 |

EXAMPLE 11

Blood Lipid Reducing Effect by a Novel *Gynostemma pentaphyllum* Extract

In order to determine the blood lipid reducing effect by the novel *Gynostemma pentaphyllum* extract, on males and females tested in Example 10, changes in the contents of blood neutral lipid and cholesterol were analyzed.

As a result, as noted in Table 8, in the group administered with TG1022F having increased damulin contents, the male group and the female group showed reduction of neutral lipid by 23.7 mg/dl and 28.4 mg/dl on the average, and reduction of total cholesterol by 26.3 mg/dl and 21.5 mg/dl on the average, respectively. Meanwhile, in the group administered with TG1022 (a simple *Gynostemma pentaphyllum* extract), the male group and the female group showed reduction of neutral lipid by 3.7 mg/dl and 4.8 mg/dl on the average, and reduction of total cholesterol by 3.1 mq/dl and 2.5 mg/dl on the average, respectively (see Table 8). Based on the result, TG1022F (a novel *Gynostemma pentaphyllum* extract with increased contents of damulin A and damulin B) was determined to have a much better blood-neutral-lipid/total-cholesterol reducing effect, compared to TG1022 (a simple *Gynostemma pentaphyllum* extract). Table 5 shows a blood lipid reducing effect in a human body by TG1022F (a novel *Gynostemma pentaphyllum* extract with a novel composition having increased contents of damulin A and damulin B, damulin A content: 0.89%, damulin B content 0.68%).

TABLE 5

| Experimental group for human body | | Amount of reduced neutral lipid (mg/dl) | Total amount of reduced cholesterol(mg/dl) |
| --- | --- | --- | --- |
| TG1022 (simple Gynostemma pentaphyllum extract) | male Female | 3.7 ± 1.7 4.8 ± 2.1 | 3.1 ± 1.0 2.5 ± 1.8 |
| TG1022F (novel Gynostemma pentaphyllum extract) | Male female | 23.7 ± 4.1 28.4 ± 5.8 | 26.4 ± 3.9 21.5 ± 3.7 |

EXAMPLE 12

Blood Glucose Level Reducing Effect by a Novel *Gynostemma pentaphyllum* Extract In order to determine the blood glucose level reducing effect by the novel *Gynostemma pentaphyllum* extract, on males and females tested in Example 10, changes in fasting glucose levels were analyzed.

As a result, as noted in Table 8, in the group administered with TG1022F (whose contents of damulin A and damulin B were increased up to 0.89%, and 0.68%, respectively), the male group and the female group showed reduction of a fasting blood glucose level by 26.4 mg/dl and 21.5 mg/dl on the average, respectively. Meanwhile, in the group administered with TG1022 (a simple *Gynostemma pentaphyllum* extract), the male group and the female group showed reduction of a fasting blood glucose level by 3.1 mq/dl and 2.5 mg/dl on the average. Based on the result, TG1022F (a novel *Gynostemma pentaphyllum* extract with increased contents of damulin A and damulin B) was determined to have a much better blood glucose level reducing effect, compared to TG1022 (a simple *Gynostemma pentaphyllum* extract). Table 6 shows a blood glucose level reducing effect in a human body by TG1022F (a novel *Gynostemma pentaphyllum* extract with increased contents of damulin A and damulin B).

TABLE 6

| Experimental group for human body | | Amount of reduced blood glucose (mg/dl) |
| --- | --- | --- |
| TG1022 (simple Gynostemma pentaphyllum extract) | Male Female | 3.1 ± 2.6 2.2 ± 1.5 |
| TG1022F (novel Gynostemma pentaphyllum extract) | Male Female | 19.6 ± 2.8 18.5 ± 1.9 |

Although an exemplary embodiment of the present invention has been described for illustrative purposes, those skilled in the art will appreciate that various modifications, additions and substitutions are possible, without departing from the scope and spirit of the invention as disclosed in the accompanying claims.

What is claimed is

1. A method for preparing a novel *Gynostemma pentaphyllum* extract having increased concentrations of damulin A and damulin B, comprising the step of:
   subjecting an ethanol extract of *Gynostemma pentaphyllum* leaves to a temperature of about 40-125° C. and a pressure of about 1.2~1100 atmospheres for 1-24 hours to obtain increased concentrations of damulin A and damulin B, which are 0.7-7% (w/w) and 0.5-6% (w/w), respectively, based on the total weight of a dry powder of the novel *Gynostemma pentaphyllum* extract.

2. The novel *Gynostemma pentaphyllum* extract for improving and treating a metabolic syndrome, which is prepared by the method of claim 1.

3. The novel *Gynostemma pentaphyllum* extract as claimed in claim 2, wherein the metabolic syndrome is obesity, diabetes or hyperlipidaemia.

4. A functional food for improving a metabolic syndrome comprising the *Gynostemma pentaphyllum* extract as claimed in claim 2, wherein the metabolic syndrome is obesity, diabetes or hyperlipidaemia.

5. The functional food as claimed in claim 4, which comprises a carrier of thermal waters, filtrated water, distilled water, aerated water, juice, yogurt, milk, or edible oil.

6. A pharmaceutical composition for improving and treating a metabolic syndrome comprising the *Gynostemma pentaphyllum* extract as claimed in claim 2, wherein the metabolic syndrome is obesity, diabetes or hyperlipidaemia.

7. The pharmaceutical composition as claimed in claim 6, which increases enzyme activity of AMP-activated protein kinase (AMPK).

8. A pharmaceutical composition for improving and treating a metabolic syndrome, comprising at least one of at least 0.7% damulin A and at least 0.5% damulin B, represented by Formula 1:

and a pharmacologically acceptable carrier or excipient, wherein the metabolic syndrome is obesity, diabetes, or hyperlipidaemia.

9. The pharmaceutical composition as claimed in claim 8, which increases enzyme activity of AMP-activated protein kinase (AMPK).

10. A novel *Gynostemma pentaphyllum* extract comprising 0.7-7% (w/w) of damulin A and 0.5-6% (w/w) of damulin B based on the total weight of a dry powder of the *Gynostemma pentaphyllum* extract.

11. A method for improving or treating a metabolic syndrome comprising administering the novel *Gynostemma pentaphyllum* extract of claim 2 to a patient in need thereof in an effective amount for improving or treating the metabolic syndrome, wherein the metabolic syndrome is obesity, diabetes or hyperlipidaemia.

12. A method for improving or treating a metabolic syndrome comprising administering the pharmaceutical composition of claim 8 to a patient in need thereof in an effective amount for improving or treating the metabolic syndrome, wherein the metabolic syndrome is obesity, diabetes or hyperlipidaemia.

13. A method for improving or treating a metabolic syndrome comprising administering the novel *Gynostemma pentaphyllum* extract of claim 10 to a patient in need thereof in an effective amount for improving or treating the metabolic syndrome, wherein the metabolic syndrome is obesity, diabetes or hyperlipidaemia.

14. Separated and purified damulin A represented by the following formula:

[Formula 1]

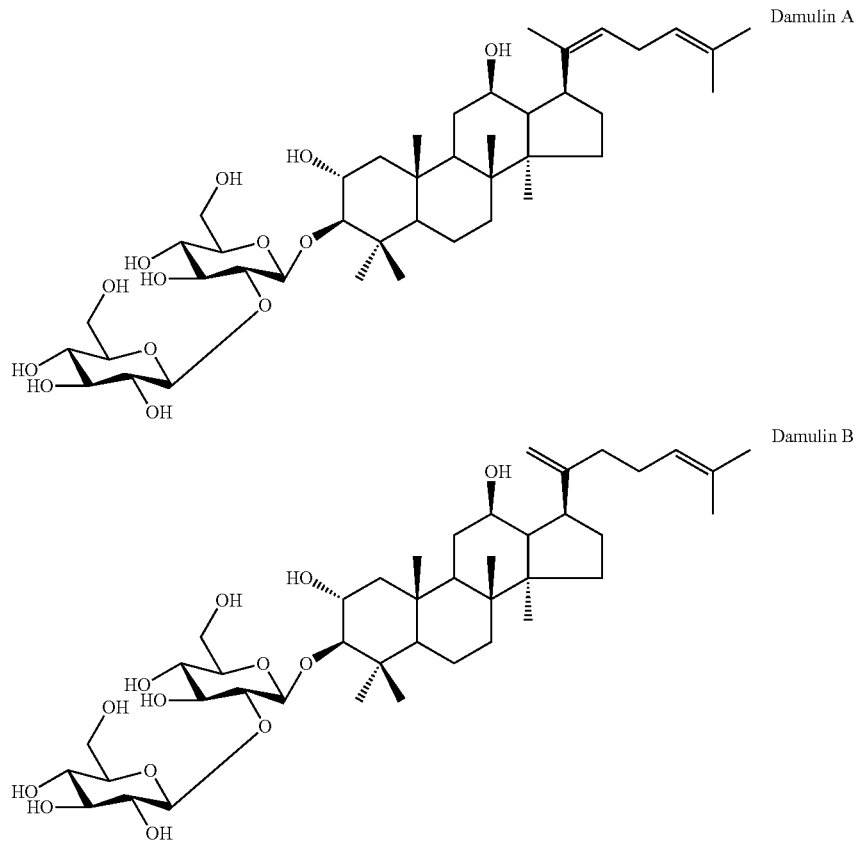

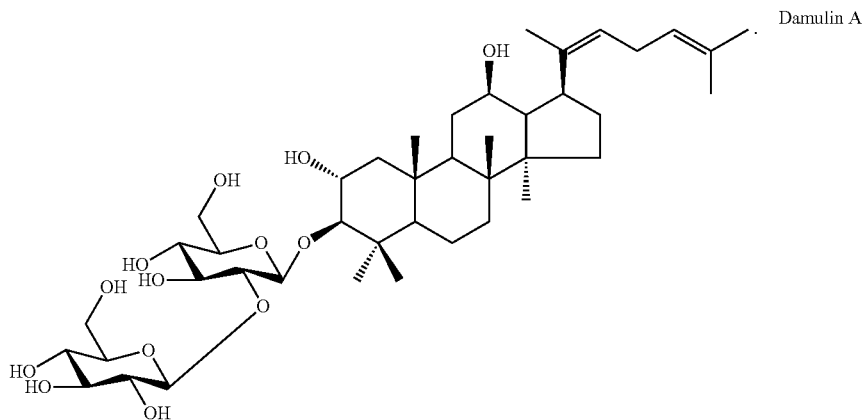
Damulin A

15. Separated and purified damulin B represented by the following formula:

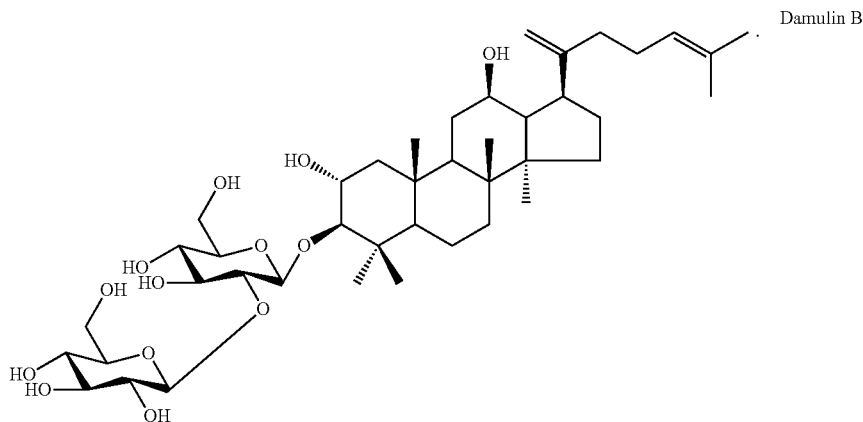
Damulin B

16. A method for improving or treating a metabolic syndrome comprising administering the separated and purified damulin A of claim 14 to a patient in need thereof in an effective amount for improving or treating the metabolic syndrome, wherein the metabolic syndrome is obesity, diabetes or hyperlipidaemia.

17. A method for improving or treating a metabolic syndrome comprising administering the separated and purified damulin B of claim 15 to a patient in need thereof in an effective amount for improving or treating the metabolic syndrome, wherein the metabolic syndrome is obesity, diabetes or hyperlipidaemia.

* * * * *

(12) INTER PARTES REVIEW CERTIFICATE (3409th)

United States Patent
Huh et al.

(10) Number: US 8,357,786 K1
(45) Certificate Issued: Feb. 7, 2024

(54) METHOD FOR PREPARING GYNOSTEMMA PENTAPHYLLUM EXTRACT WITH INCREASING DAMULIN A AND DAMULIN B CONTENTS, AND PHARMACEUTICAL COMPOSITIONS OF THE SAME FOR TREATING METABOLIC DISEASE

(75) Inventors: Tae Lin Huh; He Bok Song; Ji Eun Kim; So Young Joon; Won Keun Oh

(73) Assignee: TG BIOTECH CO., LTD.

Trial Number:

IPR2022-00998 filed May 5, 2022

Inter Partes Review Certificate for:

Patent No.: 8,357,786
Issued: Jan. 22, 2013
Appl. No.: 12/696,362
Filed: Jan. 29, 2010

The results of IPR2022-00998 are reflected in this inter partes review certificate under 35 U.S.C. 318(b).

INTER PARTES REVIEW CERTIFICATE
U.S. Patent 8,357,786 K1
Trial No. IPR2022-00998
Certificate Issued Feb. 7, 2024

AS A RESULT OF THE INTER PARTES REVIEW PROCEEDING, IT HAS BEEN DETERMINED THAT:

Claims 1-13 are found patentable.

\* \* \* \* \*